United States Patent
Gallem et al.

(10) Patent No.: US 10,376,661 B2
(45) Date of Patent: Aug. 13, 2019

(54) OPENING ELEMENT FOR OPENING AN AMPOULE IN AN AEROSOL GENERATION DEVICE AND AEROSOL GENERATION DEVICE COMPRISING THE OPENING ELEMENT

(71) Applicant: PARI Pharma GmbH, Starnberg (DE)

(72) Inventors: Thomas Gallem, Munich (DE); Uwe Hetzer, Munich (DE); Stephen Pham, San Diego, CA (US); Reynaldo Quintana, Menlo Park, CA (US)

(73) Assignee: PARI Pharma GmbH, Starnberg (DE)

( * ) Notice: Subject to any disclaimer, the term of this patent is extended or adjusted under 35 U.S.C. 154(b) by 735 days.

(21) Appl. No.: 14/427,457

(22) PCT Filed: Sep. 9, 2013

(86) PCT No.: PCT/EP2013/068592
§ 371 (c)(1),
(2) Date: Mar. 11, 2015

(87) PCT Pub. No.: WO2014/040947
PCT Pub. Date: Mar. 20, 2014

(65) Prior Publication Data
US 2015/0238712 A1    Aug. 27, 2015

(30) Foreign Application Priority Data
Sep. 12, 2012   (EP) .................................. 12184036

(51) Int. Cl.
*A61M 15/00*   (2006.01)

(52) U.S. Cl.
CPC ........ *A61M 15/004* (2014.02); *A61M 15/009* (2013.01); *A61M 15/0028* (2013.01);
(Continued)

(58) Field of Classification Search
CPC ..... A45F 2005/008; A45F 5/00; A61K 47/10; A61K 47/12; A61K 47/183; A61K 47/20;
(Continued)

(56) References Cited

U.S. PATENT DOCUMENTS

| 3,425,414 A |   | 2/1969 | Roche |
| 4,995,385 A | * | 2/1991 | Valentini ........... A61M 15/0028 128/203.15 |

(Continued)

FOREIGN PATENT DOCUMENTS

| CN | 1330563 A | 1/2002 |
| CN | 1516606 A | 7/2004 |

(Continued)

OTHER PUBLICATIONS

Extended Search Report from corresponding European Application No. 12184036.7 dated Dec. 6, 2012.
(Continued)

*Primary Examiner* — Annette Dixon
(74) *Attorney, Agent, or Firm* — Wolf, Greenfield & Sacks, P.C.

(57) ABSTRACT

An opening element for opening an ampoule in an aerosol generation device includes a first member which has a conduit extending therethrough for guiding a fluid contained in the ampoule through the first member and a second member which is arranged at least partly inside or on the conduit. Further, an aerosol generation device includes such an opening element.

20 Claims, 3 Drawing Sheets

(52) U.S. Cl.
CPC ..... *A61M 15/0036* (2014.02); *A61M 15/0085* (2013.01); *A61M 2202/0007* (2013.01); *A61M 2202/0468* (2013.01); *A61M 2205/02* (2013.01)

(58) Field of Classification Search
CPC ...... A61K 47/26; A61K 47/40; A61K 9/0073; A61K 9/0075; A61K 9/19; A61M 11/00; A61M 11/001; A61M 11/002; A61M 11/005; A61M 11/007; A61M 11/04; A61M 11/042; A61M 15/00; A61M 15/0015; A61M 15/0016; A61M 15/0018; A61M 15/0023; A61M 15/0026; A61M 15/0028; A61M 15/0031; A61M 15/0033; A61M 15/0035; A61M 15/0036; A61M 15/004; A61M 15/0041; A61M 15/0043; A61M 15/0045; A61M 15/0048; A61M 15/0051; A61M 15/0065; A61M 15/0071; A61M 15/0076; A61M 15/0085; A61M 15/0086; A61M 15/009; A61M 15/0091; A61M 15/025; A61M 16/0093; A61M 16/06; A61M 16/1065; A61M 16/183; A61M 2202/0208; A61M 2202/064; A61M 2205/073; A61M 2205/075; A61M 2205/276; A61M 2205/60; A61M 2209/082; A61M 2209/088; A61M 5/32; B05B 15/025; B05B 17/0607
USPC ............. 128/202.17, 203.12, 203.15, 203.21
See application file for complete search history.

(56) References Cited

U.S. PATENT DOCUMENTS

| | | | |
|---|---|---|---|
| 5,950,619 A * | 9/1999 | van der Linden | A61M 15/0065 128/200.14 |
| 5,957,389 A | 9/1999 | Wunderlich et al. | |
| 5,970,974 A * | 10/1999 | Van Der Linden | A61M 15/0065 128/200.14 |
| 6,543,443 B1 * | 4/2003 | Klimowicz | A61M 15/0085 128/200.14 |
| 6,880,555 B1 | 4/2005 | Brunnberg et al. | |
| 7,611,072 B2 | 11/2009 | Peters et al. | |
| 7,735,485 B2 | 6/2010 | Yamashita et al. | |
| 7,954,486 B2 * | 6/2011 | Papania | A61M 15/0065 128/200.14 |
| 8,596,264 B2 | 12/2013 | Sommer | |
| 8,656,908 B2 * | 2/2014 | Papania | A61M 15/0065 128/200.14 |
| 2002/0129812 A1 * | 9/2002 | Litherland | A61M 11/005 128/200.14 |
| 2003/0049396 A1 | 3/2003 | Oles et al. | |
| 2004/0031485 A1 | 2/2004 | Rustad et al. | |
| 2005/0161041 A1 | 7/2005 | Schuler et al. | |
| 2006/0207591 A1 * | 9/2006 | Gallem | A61M 11/005 128/200.14 |
| 2006/0289002 A1 * | 12/2006 | Hetzer | A61M 11/02 128/200.14 |
| 2007/0031639 A1 | 2/2007 | Hsu et al. | |
| 2007/0076067 A1 * | 4/2007 | Hamano | A61M 15/00 347/86 |
| 2007/0151562 A1 | 7/2007 | Jones et al. | |
| 2007/0154407 A1 | 7/2007 | Peters et al. | |
| 2008/0060640 A1 * | 3/2008 | Waldner | A61M 15/0085 128/200.16 |
| 2008/0299049 A1 * | 12/2008 | Stangl | A61M 15/0085 424/45 |
| 2009/0013994 A1 | 1/2009 | Jones et al. | |
| 2009/0137950 A1 | 5/2009 | Loenner et al. | |
| 2009/0223515 A1 * | 9/2009 | Watanabe | A61M 11/00 128/203.15 |
| 2009/0293868 A1 * | 12/2009 | Hetzer | A61M 15/0085 128/200.14 |
| 2010/0006113 A1 | 1/2010 | Urtsev et al. | |
| 2010/0083963 A1 | 4/2010 | Wharton et al. | |
| 2011/0114090 A1 | 5/2011 | Piper | |
| 2017/0143915 A1 | 5/2017 | Strange et al. | |
| 2017/0224937 A1 | 8/2017 | Schuschnig et al. | |

FOREIGN PATENT DOCUMENTS

| | | |
|---|---|---|
| CN | 1960777 A | 5/2007 |
| CN | 101547717 A | 9/2009 |
| DE | 20006010 U1 | 7/2000 |
| DE | 10 2005 057 685 A1 | 6/2007 |
| EP | 0 786 263 A2 | 7/1997 |
| EP | 1 040 874 A2 | 10/2000 |
| EP | 1142600 A1 | 10/2001 |
| EP | 2 062 608 A2 | 5/2009 |
| JP | H05-200329 A | 8/1993 |
| JP | H10-237 A | 1/1998 |
| JP | 2000-336194 A | 12/2000 |
| JP | 2013-48935 A | 3/2013 |
| WO | WO 99/04840 A1 | 2/1999 |
| WO | WO 99/42154 A1 | 8/1999 |
| WO | WO 01/26720 A1 | 4/2001 |
| WO | WO 01/56639 A1 | 8/2001 |
| WO | WO 01/74672 A1 | 10/2001 |
| WO | WO 01/87393 A2 | 11/2001 |
| WO | WO 03/061745 A1 | 7/2003 |
| WO | WO 05/030305 A1 | 4/2005 |
| WO | WO 2006/006963 A2 | 1/2006 |
| WO | WO 2011/0546931 | 5/2011 |
| WO | WO 2013/030117 A2 | 3/2013 |

OTHER PUBLICATIONS

International Search Report and Written Opinion for corresponding International Application No. PCT/EP2013/068592 dated Nov. 7, 2013.

English translation of Chinese Examination Report from corresponding Chinese Application No. 201380047513.1 dated Oct. 5, 2016.

Chinese Search Report dated Jan. 3, 2018 in connection with Chinese Application No. 201380047513.1 and English translation thereof.

International Preliminary Report on Patentability for corresponding International Application No. PCT/EP2013/068592 dated Mar. 17, 2015.

International Preliminary Report on Patentability dated Feb. 9, 2017 in connection with International Application No. PCT/EP2015/060454.

International Search Report and Written Opinion dated Jul. 8, 2015 in connection with International Application No. PCT/EP2015/060454.

Japanese Notice of Grounds of Rejection dated Nov. 20, 2018 in connection with Japanese Application No. 2017-505162.

Kharitonov et al., Surface modification of polymers by direct fluorination: A convenient approach to improve commercial properties of polymeric articles. Pure Appl. Chem. 2009; 81(3):451-471.

Lee et al., The Wettability of Fluoropolymer Surfaces: Influence of Surface Dipoles. Langmuir. 2008; 24:4817-4826.

* cited by examiner

OPENING ELEMENT FOR OPENING AN AMPOULE IN AN AEROSOL GENERATION DEVICE AND AEROSOL GENERATION DEVICE COMPRISING THE OPENING ELEMENT

CROSS REFERENCE TO RELATED APPLICATIONS

This application is a national stage of PCT/EP2013/068592, filed Sep. 9, 2013, which claims priority to European Patent Application No. 12184036.7, filed Sep. 12, 2012, which are hereby incorporated herein by reference in their entirety.

FIELD OF THE INVENTION

The invention relates to an opening element for opening an ampoule in an aerosol generation device (nebuliser) and an aerosol generation device comprising this opening element.

BACKGROUND ART

Aerosols for therapeutic purposes are generated with aerosol generation devices. A fluid (i.e., medicament) to be nebulised is stored in an ampoule that can be inserted in the aerosol generation device. The inserted ampoule is opened with an opening element, such as a collar, cannula or hollow needle, provided in the aerosol generation device and the medicament stored in the ampoule is guided through the opening element into the device, where it is nebulised. A conventional aerosol generation device of this type is disclosed, for example, in US-A-2009/0293868.

The requirements placed on the aerosol generation device arise from the treatment to be performed with the aerosols. One of the requirements concerns dosage accuracy and precision, i.e., the accuracy and precision of the administered quantity of the medicament provided as an aerosol. Only if the dose of a medicament administered to a patient (user) is precisely established, a precise and effective treatment with highly effective medicaments can be carried out. One of the basic conditions influencing dosage accuracy and precision is the quantity of fluid to be nebulised that is guided from the ampoule into the aerosol generation device.

Known opening elements are made from materials having poor wetting characteristics, such as Grilamid resin or other materials, like plastic materials, with a higher contact angle or surface adhesion. The hydrophobicity or other features of these materials can impede the fluid released from the ampoule from draining through the opening element and into the aerosol generation device. The aerosol generation device cannot aerosolise the fluid from the ampoule unless the fluid comes into contact with an aerosol generating element of the device, such as a vibrating membrane with through holes. Any fluid that remains suspended in the opening element, rather than draining therethrough into the aerosol generation device, will not be aerosolised, thus leading to undesired variations in the emitted dose of a fluid (i.e., medicament). Such dosing variations can considerably compromise the effectiveness of the aerosol application (i.e., aerosol treatment).

A conventional opening element is disclosed, for example, in US-A-2009/0137950.

SUMMARY OF THE INVENTION

One object of the invention is to provide an opening element for opening an ampoule in an aerosol generation device which allows for a controlled fluid flow through the element, thus enabling a high aerosol dosage precision. Further, the invention aims to provide an aerosol generation device comprising such an opening element.

The invention provides an opening element for opening an ampoule in an aerosol generation device, the opening element comprising a first member which has a conduit or channel extending therethrough for guiding a fluid contained in the ampoule through the first member and a second member which is arranged at least partly inside or on the conduit or channel.

The surface of the first member defining (forming, delimiting) the conduit or channel is an inner surface of the first member.

Since, in the opening element of the invention, at least a portion of a surface of the second member comes in contact with the fluid to be drained, the second member thereby provides additional surface area for the fluid to be discharged from the ampoule.

In this way, a controlled and constant fluid flow from the ampoule through the conduit of the first member and into the aerosol generation device can be achieved, thus reliably preventing the occurrence of variations in the total emitted aerosol dose. Moreover, the formation of gas bubbles, such as air bubbles, adhering in the conduit can be prevented. Further, even if a gas bubble is formed in a lower portion of the opening element (i.e., a portion of the element at the side of the aerosol generation device) during opening of the ampoule, the second member can guide the fluid past the gas bubble into the aerosol generation device by gravitational force, thus ensuring an uninterrupted fluid flow through the opening element.

At least a portion of a surface of the second member may be arranged at least partly inside the conduit. The entire surface of the portion of the second member which is arranged inside the conduit may have the same degree of hydrophilicity as or a higher or lower degree of hydrophilicity than the surface of the first member defining the conduit. In this way, a particularly steady flow of the fluid through the conduit can be achieved. The entire surface of the second member may be more hydrophilic than the surface of the first member defining the conduit.

At least a portion of a surface of the second member may be more wettable (hydrophilic) than a surface of the first member defining the conduit. In this way, the drainage characteristics of the second member can be further enhanced. Since, in this case, at least a portion of a surface of the second member is more wettable than the surface of the first member defining the conduit, a more hydrophilic path for a fluid flowing through the conduit is provided, thus significantly reducing the probability of the fluid being suspended in the conduit. In particular, a fluid which comes into contact with the more wettable surface portion of the second member wets the surface portion and flows along the portion through the conduit towards the aerosol generation device.

As used herein, the term "more wettable" (more hydrophilic) defines that at least a portion of a surface of the second member has a higher degree of wettability than the surface of the first member defining the conduit. The wettability of a solid surface by a fluid is quantified by the contact angle. The contact angle is defined as the angle at which a fluid (e.g., a liquid or a vapour) interface meets the solid surface. In the opening element of the invention, at least a portion of a surface of the second member may have a smaller contact angle than the surface of the first member defining the conduit. The contact angle of the at least a portion of a surface of the second member may be 5° or more, 10° or more, 20° or more, 30° or more, 40° or more or 50° or more smaller than the contact angle of the surface of the first member defining the conduit.

The at least a portion of a surface of the second member may be made more wettable (hydrophilic) by providing it with a hydrophilic surface structure or surface adhesion, e.g., by surface treatment, such as etching, e.g., plasma etching, polishing, gas ($O_2$) treatment, coating, surface preparation or the like. Moreover, the second member may be made of a material which is more wettable (hydrophilic) than a material of the first member. Such a configuration of the opening element has the advantage, e.g., over opening elements which are uniformly made of a single material, that the first member may be fabricated from an easily formable material, such as a polymer, providing a high degree of freedom in designing the opening element and enabling a simple and cost efficient manufacturing process of the opening element, e.g., by injection moulding, lock in place or the like. In the first line, the invention stabilises and secures the fluid drain off from the ampoule to the aerosol generating element.

The opening element of the invention is particularly advantageous for use with ampoules with small openings for the discharge of the contents, having small amounts of fluid stored therein, such as 50 ml or less, since, in this case, gas bubbles are frequently formed in the lower portion of conventional opening elements during opening of the ampoule. Therapeutic aerosol generating devices normally use reservoirs or ampoules having small amounts of fluid stored therein, such as 20 ml or less, preferred equal or less than 10 ml and most preferred equal or less than 8 ml.

Herein, the term "ampoule" refers to any type of container, blister or reservoir in which a fluid, e.g., a fluid containing a medicament or active compound, can be stored. An ampoule can be made of various materials, for example, plastic, glass, ceramic, metal or other suitable materials. In particular, an ampoule can also consist of different or same materials in sections or in combinations, like sandwich materials. For example, a glass ampoule can be sealed with a plastic seal or different areas of the ampoule can be made of different plastics which are accordingly selected depending on their use at the corresponding ampoule areas. The first element may be a collar, a jacket or any other type of annular body.

The opening element of the invention may be used with any type of aerosol generation device, aerosol delivery device, aerosol inhalation device, medical aerosol device, aerosol diagnostic device, aerosol prophylactic device, aerosol therapeutic device, aerosol humidification device or aerosol therapy device. In particular, the aerosol generation device may be a nebuliser, atomiser such as a humidifier, a pneumatic nebuliser, electronic nebuliser, an ultrasonic nebuliser, an electro-hydrodynamic nebuliser, an electrostatic nebuliser, a membrane nebuliser, a vibrating membrane nebuliser, e.g., an electronic vibrating membrane nebuliser, a jet nebuliser, a humidifier/nebuliser for ventilation devices or the like.

The fluid contained or stored in the ampoule may be a fluid for the generation of a pharmaceutical aerosol for the delivery of an active compound. An active compound is a natural, biotechnology-derived or synthetic compound or mixture of compounds useful for the diagnosis, prevention, management or treatment of a disease, condition or symptom of an animal, in particular a human. Other terms which may be used as synonyms of active compounds include, for example, active ingredient, active pharmaceutical ingredient, drug substance, diagnostic material, drug, medicament and the like. The fluid could be of a liquid, solution, suspension, colloidal mixture or liposomal formulation form and can be prepared, mixed or opened before or during the application.

The active compound comprised in the fluid stored in the ampoule may be a drug substance or a medicament which is useful for the prevention, management, diagnosis or treatment of any disease, symptom or condition affecting the body cavities, the abdomen, the eyes, the intestine, the stomach, the nose, the sinuses, the osteomeatal complex, the mouth, the trachea, the lungs, the bronchia, the bronchioles, the alveoli and/or the respiratory tract.

Among the active compounds which may be useful for serving one of the purposes named previously and that may be used together with the present invention, are, for example, substances selected from the group consisting of anti-inflammatory compounds, anti-infective agents, antiseptics, prostaglandins, endothelin receptor agonists, phosphodiesterase inhibitors, beta-2-sympathicomimetics, decongestants, vasoconstrictors, anticholinergics, immunomodulators, mucolytics, anti-allergic drugs, antihistaminics, mast-cell stabilizing agents, tumor growth inhibitory agents, wound healing agents, local anaesthetics, antioxidants, oligonucleotides, peptides, proteins, vaccines, vitamins, plant extracts, cholinesterase inhibitors, vasoactive intestinal peptide, serotonin receptor antagonists, and heparins, glucocorticoids, anti-allergic drugs, antioxidants, vitamins, leucotriene antagonists, anti-infective agents, antibiotics, antifungals, antivirals, mucolytics, decongestants, antiseptics, cytostatics, immunomodulators, vaccines, wound healing agents, local anaesthetics, oligonucleotides, xanthin derived agents, peptides, proteins and plant extracts. Such compound may be used in the form of a suspension, a solution, a colloidal formulation (i.e., liposomal), etc.

Examples of potentially useful anti-inflammatory compounds are glucocorticoids and non-steroidal anti-inflammatory agents such as betamethasone, beclomethasone, budesonide, ciclesonide, dexamethasone, desoxymethasone, fluoconolone acetonide, fluocinonide, flunisolide, fluticasone, icomethasone, rofleponide, triamcinolone acetonide, fluocortin butyl, hydrocortisone, hydroxycortisone-17-butyrate, prednicarbate, 6-methylprednisolone aceponate, mometasone furoate, dehydroepiandrosterone-sulfate (DHEAS), elastane, prostaglandin, leukotriene, bradykinin antagonists, non-steroidal anti-inflammatory drugs (NSAIDs), such as ibuprofen including any pharmaceutically acceptable salts, esters, isomers, stereoisomers, diastereomers, epimers, solvates or other hydrates, prodrugs, derivatives, or any other chemical or physical forms of active compounds comprising the respective active moieties.

Examples of anti-infective agents, whose class or therapeutic category is herein understood as comprising compounds which are effective against bacterial, fungal, and viral infections, i.e. encompassing the classes of antimicrobials, antibiotics, antifungals, antiseptics, and antivirals, are

- penicillins, including benzylpenicillins (penicillin-G-sodium, clemizone penicillin, benzathine penicillin G), phenoxypenicillins (penicillin V, propicillin), aminobenzylpenicillins (ampicillin, amoxycillin, bacampicillin), acylaminopenicillins (azlocillin, mezlocillin, piperacillin, apalcillin), carboxypenicillins (carbenicillin, ticarcillin, temocillin), isoxazolyl penicillins (oxacillin, cloxacillin, dicloxacillin, flucloxacillin), and amiidine penicillins (mecillinam);
- cephalosporins, including cefazolins (cefazolin, cefazedone); cefuroximes (cefuroxim, cefamandole, cefotiam), cefoxitins (cefoxitin, cefotetan, latamoxef, flomoxef), cefotaximes (cefotaxime, ceftriaxone, ceftizoxime, cefmenoxime), ceftazidimes (ceftazidime, cefpirome, cefepime), cefalexins (cefalexin, cefaclor, cefadroxil, cefradine, loracarbef, cefprozil), and cefiximes (cefixime, cefpodoxim proxetile, cefuroxime axetil, cefetamet pivoxil, cefotiam hexetil), loracarbef, cefepim, clavulanic acid/amoxicillin, Ceftobiprole;

synergists, including beta-lactamase inhibitors, such as clavulanic acid, sulbactam, and tazobactam;

carbapenems, including imipenem, cilastin, meropenem, doripenem, tebipenem, ertapenem, ritipenam, and biapenem;

monobactams, including aztreonam;

aminoglycosides, such as apramycin, gentamicin, amikacin, isepamicin, arbekacin, tobramycin, netilmicin, spectinomycin, streptomycin, capreomycin, neomycin, paromoycin, and kanamycin;

macrolides, including erythromycin, clarythromycin, roxithromycin, azithromycin, dithromycin, josamycin, spiramycin and telithromycin;

gyrase inhibitors or fluroquinolones, including ciprofloxacin, gatifloxacin, norfloxacin, ofloxacin, levofloxacin, perfloxacin, lomefloxacin, fleroxacin, garenoxacin, clinafloxacin, sitafloxacin, prulifloxacin, olamufloxacin, caderofloxacin, gemifloxacin, balofloxacin, trovafloxacin, and moxifloxacin;

tetracyclins, including tetracyclin, oxytetracyclin, rolitetracyclin, minocyclin, doxycycline, tigecycline and aminocycline;

glycopeptides, including vancomycin, teicoplanin, ristocetin, avoparcin, oritavancin, ramoplanin, and peptide 4;

polypeptides, including plectasin, dalbavancin, daptomycin, oritavancin, ramoplanin, dalbavancin, telavancin, bacitracin, tyrothricin, neomycin, kanamycin, mupirocin, paromomycin, polymyxin B and colistin;

sulfonamides, including sulfadiazine, sulfamethoxazole, sulfalene, co-trimoxazole, co-trimetrol, co-trimoxazine, and co-tetraxazine;

azoles, including clotrimazole, oxiconazole, miconazole, ketoconazole, itraconazole, fluconazole, metronidazole, tinidazole, bifonazol, ravuconazol, posaconazol, voriconazole, and ornidazole and other antifungals including flucytosin, griseofulvin, tolnaftal, naftifin, terbinafin, amorolfin, ciclopiroxolamin, echinocandins, such as micafungin, caspofungin, anidulafungin;

nitrofurans, including nitrofurantoin and nitrofuranzone;

polyenes, including amphotericin B, natamycin, nystatin, flucytosine;

other antibiotics, including tithromycin, lincomycin, clindamycin, oxazolindiones (linzezolids), ranbezolid, streptogramine A+B, pristinamycin A+B, Virginiamycin A+B, dalfopristin/quinupristin (Synercid), chloramphenicol, ethambutol, pyrazinamid, terizidon, dapson, prothionamid, fosfomycin, fucidinic acid, rifampicin, isoniazid, cycloserine, terizidone, ansamycin, lysostaphin, iclaprim, mirocin B17, clerocidin, filgrastim, and pentamidine;

antivirals, including aciclovir, ganciclovir, birivudin, valaciclovir, zidovudine, didanosin, thiacytidin, stavudin, lamivudin, zalcitabin, ribavirin, nevirapirin, delaviridin, trifluridin, ritonavir, saquinavir, indinavir, foscarnet, amantadin, podophyllotoxin, vidarabine, tromantadine, and proteinase inhibitors, siRNA based drugs;

antiseptics, including acridine derivatives, iodine-povidone, benzoates, rivanol, chlorhexidine, quarternary ammonium compounds, cetrimides, biphenylol, clorofene, and octenidine;

plant extracts or ingredients, such as plant extracts from chamomile, hamamelis, echinacea, calendula, thymian, papain, pelargonium, pine trees, essential oils, myrtol, pinen, limonen, cineole, thymol, mentol, camphor, tannin, alpha-hederin, bisabolol, lycopodin, vitapherole;

wound healing compounds including dexpantenol, allantoin, vitamins, hyaluronic acid, alpha-antitrypsin, anorganic and organic zinc salts/compounds, salts of bismuth and selen;

interferones (alpha, beta, gamma), tumor necrosis factors, cytokines, interleukines;

immunmodulators including methotrexat, azathioprine, cyclosporine, tacrolimus, sirolimus, rapamycin, mofetil; mofetil-mycophenolate.

cytostatics and metastasis inhibitors;

alkylants, such as nimustine, melphanlane, carmustine, lomustine, cyclophosphamide, ifosfamide, trofosfamide, chlorambucil, busulfane, treosulfane, prednimustine, thiotepa;

antimetabolites, e.g. cytarabine, fluorouracil, methotrexate, mercaptopurine, tioguanine;

alkaloids, such as vinblastine, vincristine, vindesine;

antibiotics, such as alcarubicine, bleomycine, dactinomycine, daunorubicine, doxorubicine, epirubicine, idarubicine, mitomycine, plicamycine;

complexes of transition group elements (e.g. Ti, Zr, V, Nb, Ta, Mo, W, Pt) such as carboplatinum, cis-platinum and metallocene compounds such as titanocendichloride;

amsacrine, dacarbazine, estramustine, etoposide, beraprost, hydroxycarbamide, mitoxanthrone, procarbazine, temiposide;

paclitaxel, gefitinib, vandetanib, erlotinib, poly-ADP-ribose-polymerase (PRAP) enzyme inhibitors, banoxantrone, gemcitabine, pemetrexed, bevacizumab, ranibizumab. Examples of potentially useful mucolytics are DNase, P2Y2-agonists (denufosol), drugs affecting chloride and sodium permeation, such as N-(3,5-Diamino-6-chloropyrazine-2-carbony)-N'-{4-[4-(2,3-dihydroxypropoxy)-phenyl]butyl}guanidine methanesulfonate (PARION 552-02), heparinoids, guaifenesin, acetylcysteine, carbocysteine, ambroxol, bromhexine, tyloxapol, lecithins, myrtol, and recombinant surfactant proteins.

Examples of potentially useful vasoconstrictors and decongestants which may be useful to reduce the swelling of the mucosa are phenylephrine, naphazoline, tramazoline, tetryzoline, oxymetazoline, fenoxazoline, xylometazoline, epinephrine, isoprenaline, hexoprenaline, and ephedrine.

Examples of potentially useful local anaesthetic agents include benzocaine, tetracaine, procaine, lidocaine and bupivacaine.

Examples of potentially useful antiallergic agents include the afore-mentioned glucocorticoids, cromolyn sodium, nedocromil, cetrizin, loratidin, montelukast, roflumilast, ziluton, omalizumab, heparinoids and other antihistamins, including azelastine, cetirizin, desloratadin, ebastin, fexofenadin, levocetirizin, loratadin.

Examples of potentially useful anticholinergic agents include ipratropium bromide, tiotropium bromide, oxitropium bromide, glycopyrrolate.

Examples of potentially useful beta-2-sympathicomimetic agents include salbutamol, fenoterol, formoterol, indacaterol, isoproterenol, metaproterenol, salmeterol, terbutaline, clenbuterol, isoetarine, pirbuterol, procaterol, ritodrine.

Examples of xanthine derived agents include theophylline, theobromine, caffeine.

Antisense oligonucleotides are short synthetic strands of DNA (or analogs) that are complimentary or antisense to a target sequence (DNA, RNA) designed to halt a biological event, such as transcription, translation or splicing. The resulting inhibition of gene expression makes oligonucleotides dependent on their composition useful for the treatment of many diseases and various compounds are currently clinically evaluated, such as ALN-RSV01 to treat the respiratory syncytical virus by, AVE-7279 to treat asthma and allergies, TPI-ASM8 to treat allergic asthma, 1018-ISS to treat cancer.

Examples of potentially useful peptides and proteins include antibodies against toxins produced by microorganisms, antimicrobial peptides such as cecropins, defensins, thionins, and cathelicidins.

The second member may be a coating provided on at least a portion of the surface of the first member defining the conduit. Further, the second member may be formed by a surface treatment or surface preparation of at least a portion of the surface of the first member defining the conduit, such as etching, e.g., plasma etching, polishing, an $O_2$ treatment, gas treatment, parylane, cathode electro-deposition coating, $SiO_2$ and $ZrO_2$ preparation, co-condensation or the like.

In one embodiment, at least a portion of the second member extends across the width of the conduit, i.e., across a diameter (in a direction perpendicular to the axial direction of the conduit) of the conduit, with its plane parallel to the axial direction of the conduit. In this case, at least a portion of the second member extends from one side of the conduit to an opposite side of the conduit. In the case of the formation of a gas bubble in the opening element, e.g., due to incomplete drainage, a small amount of fluid contained in the ampoule or a quick opening of the ampoule, this configuration of the second member helps to prevent the gas bubble from spreading over the entire cross-section of the opening element. In this way, an interruption of the fluid flow through the opening element caused by the gas bubble can be prevented in a particularly reliable and simple manner.

The second member may extend across the width of the conduit over a portion of the length of the conduit or over the entire length of the conduit.

At least a portion of the second member may extend across the entire width of the conduit with its plane parallel to the axial direction of the conduit.

At least a portion of the second member may extend along the entire length of the conduit in the axial direction of the conduit. In this way, the fluid from the ampoule can be guided through the conduit along its entire length by the second member, thereby further improving the fluid flow through the opening element. Hence, variations of the aerosol doses emitted by the aerosol generation device can be prevented in a particularly reliable manner.

In one embodiment, the second member has a substantially planar shape. As used herein, the term "substantially planar shape" defines a plate shape or a sheet shape of the second member, i.e., a shape, the lateral dimensions of which along a plane are larger than the extension thereof in a direction perpendicular to the plane at any point of the plane, wherein the perpendicular extension (thickness) does not have to be constant along the plane. However, the second member may have a plate or sheet shape with a constant thickness along the plane.

The thickness of the first or second member may be in a range from 0.01 mm to 2 mm, or more preferred in a range from 0.1 mm to 1.0 mm and most preferred in a range from 0.4 mm to 0.6 mm. A lower limit of the thickness of the first or second member may be 0.01 mm, 0.10 mm, 0.30 mm, 0.35 mm, 0.40 mm, 0.45 mm, 0.50 mm, 0.55 mm, 0.60 mm or 0.8 mm. An upper limit of the thickness of the second member may be 0.50 mm, 0.55 mm, 0.60 mm, 0.65 mm, 0.70 mm, 0.80 mm, 1.00 mm or 2 mm. A second member having a substantially planar shape can be manufactured in a particularly simple manner, e.g., by punching, die-cutting, laser-cutting or the like, thus further simplifying the fabrication process of the opening element.

Further, using a second member having such a reduced thickness provides the advantage that the free area of the conduit is not significantly reduced, so that the fluid flow through the conduit is not impeded to a significant degree.

In one embodiment, the second member partitions the conduit into at least two sections, wherein each section extends in the axial direction of the conduit. In this way, the spreading of one or more gas bubbles, which might have been formed in the opening element during opening of the ampoule, across the entire cross-section of the conduit can be prevented in a particularly reliable and simple manner. For example, the second member may be a substantially planar member which is inserted into the conduit so as to extend across the width of the conduit in one or more areas of the conduit.

In one embodiment, the second member at least partly extends along the circumference of the conduit. The second member may extend along a portion of the circumference of the conduit over a portion of the length of the conduit or over the entire length of the conduit. Further, at least a portion of the second member or the entire second member may extend along the entire circumference of the conduit or along a portion of the circumference of the conduit, e.g., over an angular range or sector of 90° or more, 180° or more, 250° or more, 300° or more or 350° or more. For example, the second member may be a sheet-shaped or sheet-like member which is rolled or folded and inserted into the conduit in its rolled or folded form, so as to at least partly extend along the circumference of the conduit.

By arranging the second member so as to at least partly extend along the circumference of the conduit, the surface of the second member inside the conduit which comes into contact with the fluid from the ampoule can be made particularly large, thus further enhancing the fluid flow through the conduit. In this way, drainage of the ampoule contents can be achieved in a particularly reliable manner.

The second member may be at least partly in contact with the surface of the first member defining the conduit. For example, 30% or more, 50% or more, 70% or more or 90% or more of the surface of the first member defining the conduit may be in contact with the second member. In particular, the second member may cover the portions of the surface of the first member defining the conduit with which it is in contact. In this way, the area of the surface of the first member defining the conduit which comes into contact with the fluid from the ampoule can be reduced, thereby enabling a particularly steady fluid flow through the opening element.

In one embodiment, the second member is resilient and arranged at least partly inside the conduit in an at least partly compressed state. In this case, the second member may be held in place inside the conduit by its restoring force. Such a configuration of the second member allows for a particularly simple structure of the opening element, since no additional means for fixing or securing the second member inside the conduit are required. For example, the second member may be a sheet of a resilient material, such as a metal, which is rolled or folded and inserted into the conduit in its rolled or folded state.

Alternatively, the second member may be a substantially planar member with one or more cut-out, opening or recess portions allowing for a compression of the member in a direction in the plane of the member and perpendicular to the axial direction of the conduit. For example, the member may have one or more cut-outs that create one or more flexible bars with one or more barbed hooks to lock into one or more grooves on the inner side of the conduit.

The thickness of the sheet member or the substantially planar member may be in the range defined above. Specifically, a lower limit of the thickness of the second member may be 0.1 mm, 0.2 mm, 0.3 mm, 0.4 mm, 0.5 mm, 0.6 mm or 0.8 mm. An upper limit of the thickness of the second member may be 0.6 mm, 0.7 mm, 0.8 mm, 0.9 mm, 1.0 mm, 1.5 mm or 2 mm.

Alternatively, the second member may be held in place inside the conduit by insert moulding (i.e., moulding the first member at least partly around the second member), gluing the second member to the first member or using fixation means, such as rivets, riveted bolts, screws, clamps or the like, for securing the second member to the first member.

The first member may have a substantially cylindrical shape. The opening element may be a thorn, a hollow needle or the like. Also, the conduit may have a substantially cylindrical shape. Alternatively, the first member and/or the conduit may have a rectangular, square, triangular or other polygonal cross-sectional shape. A substantially cylindrical shape of the first member provides the advantage of enabling a particularly uniform opening of the ampoule, thus allowing for a steady opening process. A substantially cylindrical shape of the conduit provides the advantage of allowing for a particularly homogeneous flow of the fluid through the opening element.

In one embodiment, at least a portion of the second member extends through a centre (central axis) of the conduit with its plane parallel to the axial direction of the conduit. In this case, the second member may partition the conduit into two sections with the same approximate dimensions, each extending in the axial direction of the conduit. For example, the second member may be a plate- or sheet-shaped member which is inserted into the conduit, e.g., a substantially cylindrical conduit, so that the plane of the second member passes through the centre of the conduit.

Such a central arrangement of the second member can prevent the formation or spreading of one or more gas bubbles over the entire cross-section of the conduit in a particularly reliable and efficient manner. Moreover, a homogeneous fluid flow through the conduit can be ensured.

In one embodiment, the first member has an opening portion for opening the ampoule. The opening portion may be a portion of the first member which is inclined with respect to the remainder of the first member. For example, the first member may have a substantially cylindrical shape with an inclined top surface. Further, the opening portion may be a cutting edge or the like. By providing the first member with an opening portion, the opening of the ampoule can be facilitated.

In place of or in addition to the opening portion of the first member, the second member may have an opening portion for opening the ampoule. The opening portion of the second member may be formed by a portion of the second member which protrudes beyond the first member. The opening portion of the second member may be a cutting edge or the like. In particular, if the second member is made of a robust material, such as a metal, such a cutting edge can be formed with a small thickness without compromising the stability of the member, thus enabling a particularly reliable and efficient opening of the ampoule.

In particular, by using a first member and/or a second member having an opening portion, the force required for opening the ampoule can be reduced, thus enabling a controlled and steady opening process.

As has been mentioned above, the second member may be made of a metal, such as stainless steel, e.g., stainless 316 or 316L. Metals, in particular stainless steel, offer a higher surface wettability than polymers while also possessing desirable mechanical properties for fabrication. Moreover, they have a high corrosion resistance and can be formed into structures with low wall thicknesses without compromising the stability of the second member. In particular, stainless steel 316 and 316L have an especially high degree of corrosion resistance.

The first member may be made of a polymer, such as polyamide, e.g., Grilamid, or other high performance, rigid polymers. Polymers, in particular polyamide and high performance, rigid polymers, have a high degree of formability in the molten or softened state, thus providing a high degree of freedom in designing the first member and allowing for a simple and cost efficient fabrication of the member, e.g., by injection moulding or the like. A silicone or other soft material may be used as a sealing element and may be produced by a two component injection moulding process.

The opening element may further comprise one or more valve flaps for controlling the transport of a gas, such as air, e.g., ambient air, into the aerosol generation device. The one or more valve flaps may be hingedly attached to the first member so as to allow pivoting thereof towards and away from the first member. During an inhalation manoeuvre, the one or more valve flaps may open, so as to allow a gas, such as ambient air, to flow into the aerosol generation device. In this way, an aerosol generated by an aerosol generating element of the aerosol generation device can be delivered to a user or patient together with the gas introduced into the device. For example, during exhalation by the patient, the one or more valve flaps may close, thus reliably avoiding any undesired transport of aerosol outside the device. Hence, any loss of aerosol can be reliably prevented.

The invention further provides an aerosol generation device comprising the opening element of the invention. The opening element is in fluid communication with an aerosol generating element, such as a nozzle, a vibrating membrane or a perforated vibrating membrane with openings of the aerosol generation device, thus allowing for a controlled fluid flow from the ampoule through the opening element onto the aerosol generating element. The fluid supplied from the ampoule is aerosolised by the aerosol generating element and the aerosol thus generated is transported to a user or patient.

The opening element may be integrally formed with the aerosol generation device, e.g., by injection moulding. Alternatively, the opening element may be attached to the aerosol generation device by fixation means, such as adhesives, clamps, rivets, riveted bolts, screws or the like. The aerosol generation device according to the invention provides the advantageous effects already described in detail above for the opening element of the invention. In particular, the aerosol generation device of the invention allows for a controlled fluid flow from the ampoule to the aerosol generating element, thus achieving a high degree of reliability in the draining of the ampoule.

BRIEF DESCRIPTION OF THE DRAWINGS

Hereinafter, non-limiting examples of the invention are explained with reference to the drawings, in which:

FIGS. 2(a) and (b) show schematic views of an opening element according to a second embodiment of the present invention, wherein FIG. 2(a) is a perspective view of the opening element and FIG. 2(b) a side view of the opening element;

FIGS. 3(a) to (d) show schematic views of an opening element according to a third embodiment of the present invention, wherein FIG. 3(a) is a perspective view of the opening element, FIG. 3(b) is a bottom view of the opening element, FIG. 3(c) is a cross-sectional view of the opening element in a plane parallel to the plane of the second member and FIG. 3(d) is a cross-sectional view of the opening element in a plane perpendicular to the plane of the second member;

FIGS. 4(a) and (b) show schematic views of an opening element according to a fourth embodiment of the present invention, wherein FIG. 4(a) is a perspective view of the second member of the opening element, the left-hand side of FIG. 4(b) is a cross-sectional view of the opening element in a plane parallel to the plane of the lower portion of the second member and the right-hand side of FIG. 4(b) is a side view of the opening element.

DETAILED DESCRIPTION OF CURRENTLY PREFERRED EMBODIMENTS

FIGS. 1(a) and (b) show schematic views of an opening element 1 according to a currently preferred first embodiment.

Figure 1:
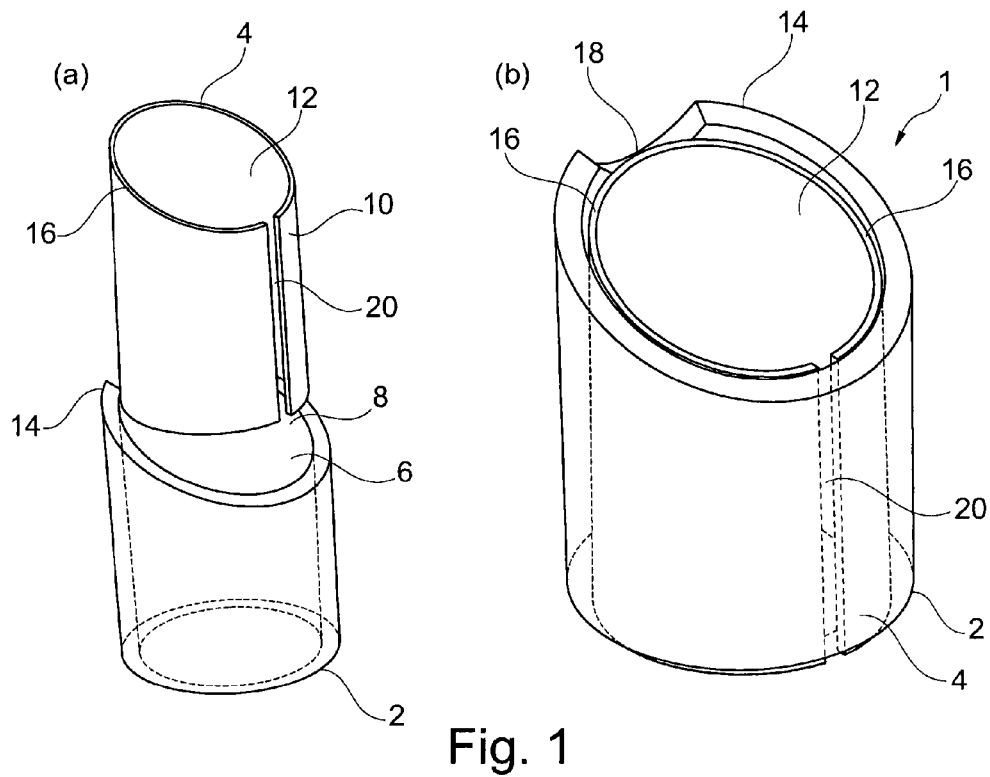
FIGS. 1(a) and (b) show schematic views of an opening element according to a first embodiment of the present invention before (FIG. 1(a)) and after (FIG. 1(b)) arranging the second member inside the conduit of the first member.

The opening element 1 shown in FIG. 1 comprises a collar 2 made of a polymer, such as polyamide, e.g., Grilamid or a high-performance polymer, as the first member and a sleeve 4 as the second member. The collar 2 is shown in transparent form for better visibility of the inner structure of the opening element 1.

The collar 2 has a conduit 6 extending therethrough for guiding a fluid contained in an ampoule through the collar 2. Both the collar 2 and the conduit 6 have a substantially cylindrical shape. The sleeve 4 is formed of a sheet of metal, such as stainless steel, which is rolled so as to assume a substantially cylindrical shape and inserted into the conduit 6 of the collar 2. The sleeve 4 is shown in FIG. 1(a) before insertion into the conduit 6 and in FIG. 1(b) after insertion into the conduit 6.

As can be seen from FIG. 1(b), the sleeve 4 extends almost along the entire circumference of the conduit 6 and is in contact with almost the entire inner surface 8 of the collar 2 which defines the conduit 6. Since the sleeve 4 is made of a resilient material, i.e., a metal, and arranged inside the conduit 6 in a compressed state, it is held within the conduit 6 by its restoring force. The restoring force of the sleeve 4 presses an outer surface 10 of the sleeve 4 against the inner surface 8 of the collar 2 defining the conduit 6, thus securely holding the sleeve 4 in its position by friction between these two surfaces 8, 10. Hence, no additional fixation means, such as adhesives, clamps, rivets, riveted bolts, screws or the like, are necessary and the opening element 1 can be formed with a simple structure.

Since the sleeve 4 is formed of a material, i.e., a metal, which is more wettable (hydrophilic) than the material of the collar 2, i.e., a polymer, an inner surface 12 of the sleeve 4 is more wettable (hydrophilic) than the inner surface 8 of the collar 2 defining the conduit 6. The inner surface 12 of the sleeve 4, which covers almost the entire inner surface 8 of the collar 2 defining the conduit 6, provides a more wettable (hydrophilic) path for a fluid from an ampoule, thus greatly reducing the probability of the fluid being suspended in the collar 2. Hence, a controlled fluid flow through the opening element 1 and into the aerosol generation device can be ensured.

As can be seen from FIGS. 1(a) and 1(b), the collar 2 has an inclined top portion 14 which is inclined with respect to the cylindrical remainder of the collar 2. The inclined top portion 14 gives the collar 2 a needle-like structure and serves as an opening portion for opening an ampoule, as will be discussed in detail below with reference to FIG. 5.

Further, also the sleeve 4 has an inclined top portion 16 following the contours of the inclined top portion 14 of the collar 2.

The inclined top portion 14 of the collar 2 has a cut-out or recess portion 18 which facilitates assembling of the sleeve 4 into or on the conduit 6 of the collar 2, thus may include a barbed hook to avoid disassembling of the sleeve 4 of the opening element 1.

The sheet of the sleeve 4 has a thickness in the range from 0.1 to 1 mm, so that the free area of the conduit 6 is not significantly reduced. The collar 2 has a wall thickness in the range from 0.4 mm to 3 mm and the conduit 6 has a diameter in the range from 4 to 20 mm.

As can be seen from FIG. 1(b), a small gap 20 exists between the two end portions of the metal sheet forming the sleeve 4. Alternatively, the sheet forming the sleeve 4 may be configured so that the end portions thereof substantially abut each other in the rolled state of the sheet, thereby eliminating the gap 20 and covering the entire inner surface 8 of the collar 2 forming the conduit 6.

FIGS. 2(a) and (b) show schematic views of an opening element 50 according to a currently preferred second embodiment of the present invention.

Figure 2:
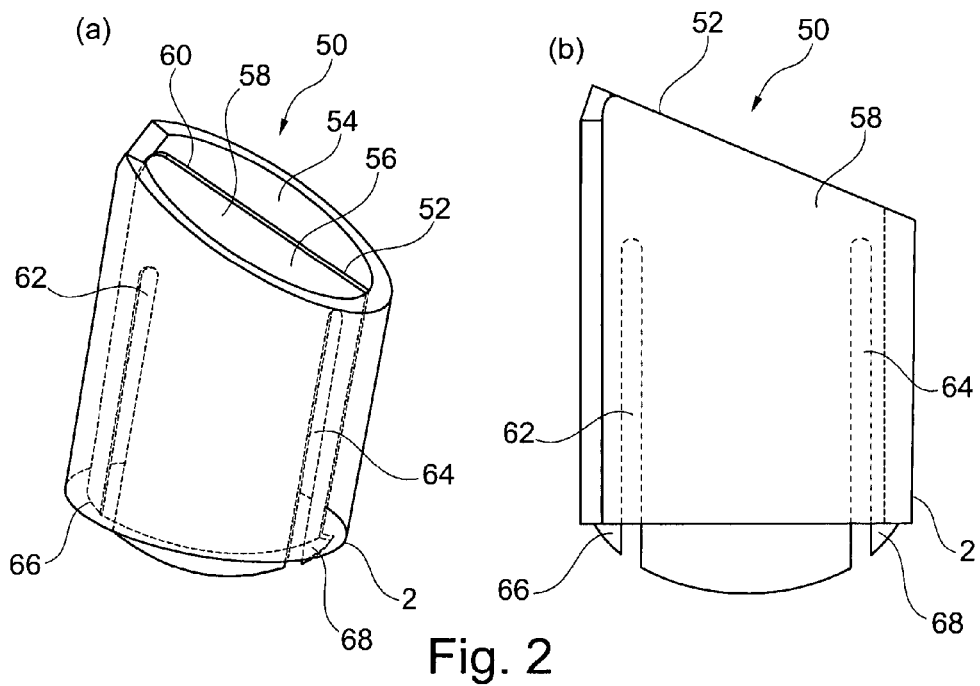

The opening element 50 shown in FIGS. 2(a) and (b) comprises a collar 2 as the first member and a plate 52 having a substantially planar shape as the second member. The structure of the collar 2 is identical to that of the collar 2 of the opening element 1 shown in FIGS. 1(a) and (b). Therefore, a detailed description thereof is omitted and the same reference signs as for the collar 2 of the opening element 1 are used. As in FIG. 1, the collar 2 is shown in FIG. 2 in transparent form for improved visibility of the inner structure of the opening element 50.

The plate 52 extends across the width of the cylindrical conduit 6 of the collar 2 with its plane parallel to the axial direction of the conduit 6 over the entire length of the conduit 6, as is shown in FIGS. 2(a) and (b). The plate 52 extends through the centre of the cylindrical conduit 6 with its plane parallel to the axial direction of the conduit 6, thus partitioning the conduit 6 into two sections 54, 56 which have the same approximate dimensions and extend in the axial direction of the conduit 6. Due to this structure of the opening element 50, a spreading of one or more gas bubbles formed during opening of the ampoule over the entire cross-section of the conduit 6 can be reliably prevented.

The plate 52 is made of a metal, such as stainless steel, whereas the collar 2 is made of a polymer, such as polyamide or a high-performance polymer, as has been discussed above. Hence, a front surface 58 and a back surface 60 of the plate 52 are more wettable (hydrophilic) than the surface 8 of the collar 2 defining the conduit 6. Thus, the plate 52 provides a more wettable (hydrophilic) path for a fluid flowing through the opening element 50, greatly improving fluid drainage from an ampoule through the collar 2. Specifically, a fluid flowing from an ampoule wets the surfaces 58, 60 of the plate 52 and flows along the plate 52 towards the aerosol generation device. Hence, a controlled fluid flow through the opening element 50 can be ensured.

Alternatively, the plate 52 may be made of a material which has the same degree of hydrophilicity as the collar 2 or a lower degree of hydrophilicity than the collar 2. Also in this case, the fluid drainage from an ampoule through the collar 2 would be improved as compared to a collar without a plate, due to the additional surface area for the fluid to be discharged which is provided by the plate 52.

The plate 52 has two cut-out or recess portions 62, 64 extending from an end of the plate 52 along the axial direction of the plate 52, i.e., along the axial direction of the conduit 6. Upon insertion of the plate 52 into the conduit 6, the plate 52 is resiliently compressed in the area of the cut-out or recess portions 62, 64 and thus securely held in its position inside the conduit 6 by its restoring force. Therefore, no additional fixation means, such as adhesives, clamps, rivets, riveted bolts, screws or the like, are necessary.

The lower portion of the plate 52 extends beyond the collar 2 and has two engaging or hook portions 66, 68 arranged at its lateral edges. These engaging or hook portions 66, 68 engage a bottom surface of the collar 2, as is schematically shown in FIGS. 2(a) and 2(b), thus reliably preventing any movement of the plate 52 in the axial direction of the conduit 6 towards the side of the ampoule. The top portion of the plate 52 is inclined, wherein the angle of inclination is approximately the same as that of the inclined top portion 14 of the collar 2 (see FIG. 2(b)).

The collar 2 of the opening elements 1, 50 of the first and second embodiments may be integrally formed with a body of the aerosol generation device, e.g., by injection moulding. Alternatively, the collar 2 may be attached to the body of the aerosol generation device by fixation means, such as adhesives, clamps, rivets, riveted bolts, screws or the like.

FIGS. 3(a) to (d) show schematic views of an opening element 50' according to a currently preferred third embodiment of the present invention.

The opening element 50' comprises a collar 2 as the first member and a plate 52 as the second member. The structures of the collar 2 and the plate 52 are the same as those of the collar 2 and the plate 52 of the opening element 50 shown in FIGS. 2(a) and (b). Hence, a detailed description thereof is omitted and the same reference signs are used.

The opening element 50' of the third embodiment differs from the opening element 50 of the second embodiment in that it further comprises an attachment structure 70 for attaching the opening element 50' to an aerosol generation device.

Figure 3:
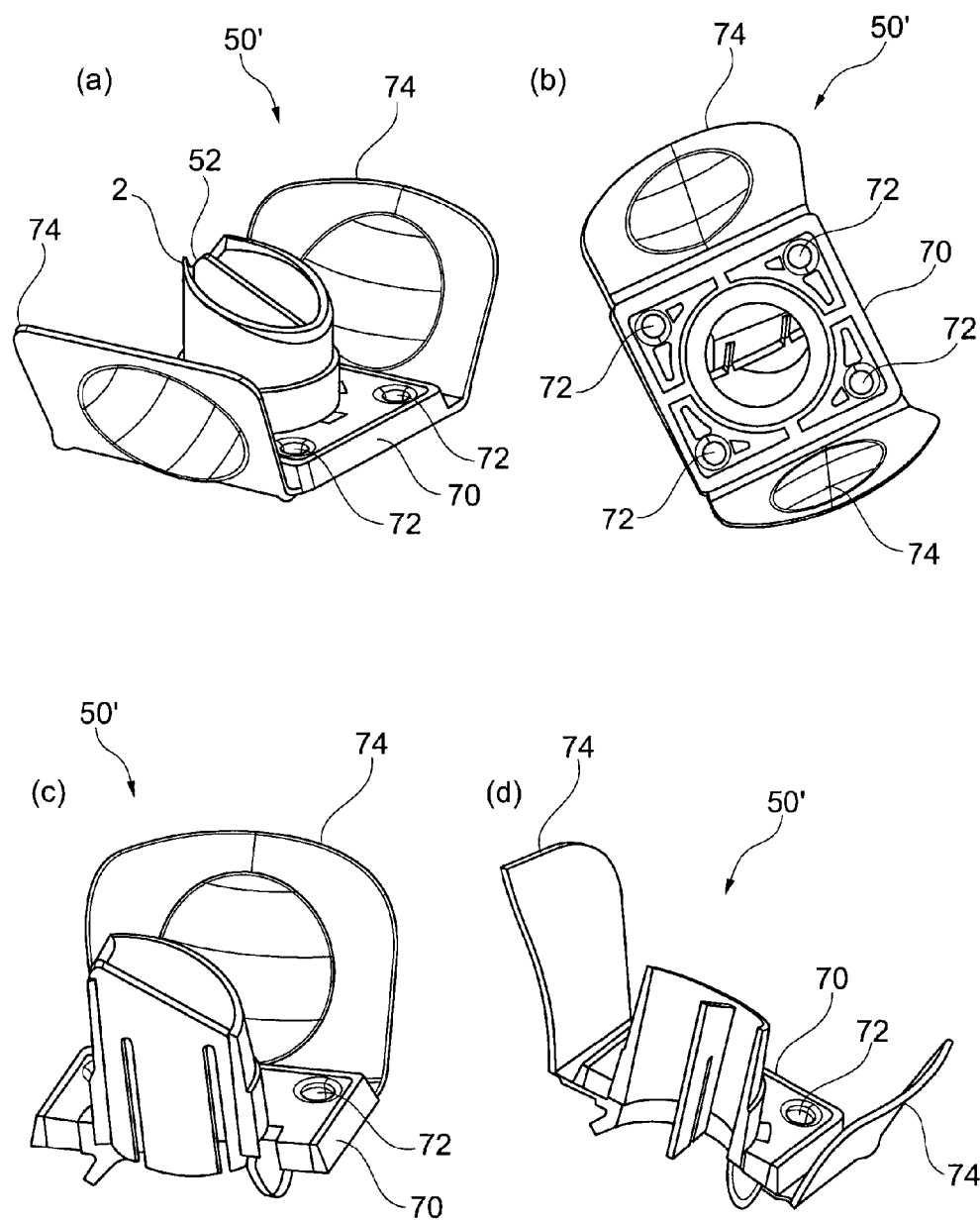

As can be seen from FIG. 3, the attachment structure 70 comprises four through holes 72, enabling attachment of the opening element 50' to the aerosol generation device by attachment means, such as screws or the like, and a pair of valve flaps 74. The valve flaps 74 are hingedly attached to the remainder of the attachment structure 70 so as to allow pivoting thereof towards and away from the collar 2. During an inhalation manoeuvre of a patient, the valve flaps 74 open, so as to allow ambient air to flow into the aerosol generation device. In this way, an aerosol generated by an aerosol generating element of the aerosol generation device can be supplied to a patient together with the air introduced into the device. However, during exhalation by the patient, the valve flaps 74 close, thus reliably avoiding any undesired transport of aerosol outside the device. Hence, any loss of aerosol can be reliably prevented.

Figure 4:
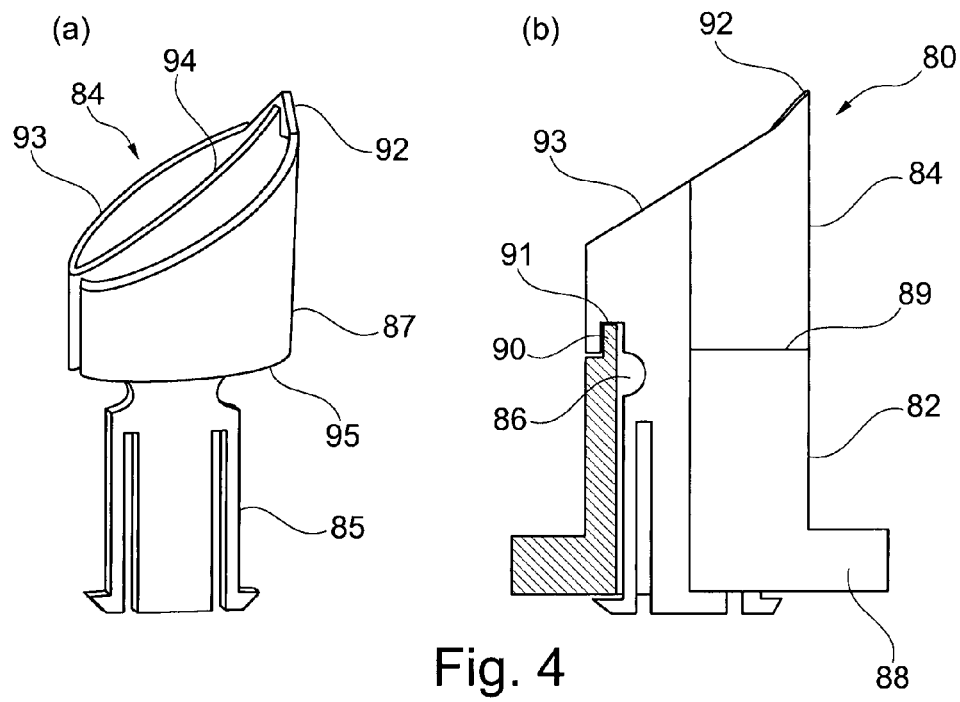

FIG. 4(b) shows a schematic view of an opening element 80 according to a currently preferred fourth embodiment of the present invention. The right-hand side of FIG. 4(b) shows a side view of the opening element 80, while the left-hand side of FIG. 4(b) shows a cross-sectional view of the opening element 80.

The opening element 80 shown in FIG. 4(b) comprises a collar 82 as the first member and a second member 84. A perspective view of the second member 84 is shown in FIG. 4(a).

The collar 82 is made of a polymer, such as polyamide, e.g., Grilamid or a high performance material, and has a substantially cylindrical shape. The collar 82 differs from the collar 2 of the opening elements 1, 50, 50' of the first to third embodiments in that it has a base portion 88 with an enlarged diameter and a substantially flat top portion 89, which is non-inclined, with a protrusion 90. A substantially cylindrical conduit 86 extends through the collar 82 for guiding a fluid contained in an ampoule through the collar 82.

The second member 84 is made of a metal, such as stainless steel. As can be seen from FIG. 4(a), the second member 84 has a lower portion 85 and an upper portion 87. The lower portion 85 of the second member 84 has a substantially planar plate shape which is substantially the same as that of the plate 52 of the opening elements 50, 50' shown in FIGS. 2 and 3.

The upper portion 87 of the second member 84 has a substantially cylindrical shape with an inclined top surface 93 and a substantially planar plate portion 94 extending across the width of the upper portion 87 through the centre thereof with its plane parallel to the axial direction of the second member 84. The outer diameter of the substantially cylindrical upper portion 87 is substantially identical to the outer diameter of the cylindrical portion of the collar 82, as is schematically shown in FIG. 4(b).

In the assembled state of the opening element 80, only the lower portion 85 of the second member 84 is, at least partly, arranged inside the conduit 86, while the upper portion 87 of the second member 84 is arranged above the substantially flat top portion 89 of the collar 82. As is schematically shown in FIG. 4(b), a bottom surface 95 of the upper portion 87 rests on, i.e., abuts, the substantially flat top portion 89 of the collar 82 and the protrusion 90 of the collar 82 is received within a corresponding recess 91 formed in the upper portion 87 of the second member 84.

Since the second member 84 is made of a more wettable material, i.e., a metal, than the collar 82, a controlled flow of fluid through the opening element 80 can be ensured. Specifically, the surfaces of the second member 84 which come into contact with a fluid from an ampoule have a higher degree of wettability than an inner surface of the collar 82 defining the conduit 86, thus reliably guiding a fluid contained in the ampoule through the collar 82 and towards the aerosol generation device.

As is schematically shown in FIGS. 4(a) and (b), the inclined top surface 93 of the upper portion 87 of the second member 84 comprises a spike portion 92 arranged at the top end of the inclined top surface 93 of the upper portion 87. The inclined top surface 93 of the upper portion 87 of the second member 84 serves as an opening portion for opening an ampoule, wherein the opening process is facilitated by the presence of the spike portion 92 which is configured so that it can penetrate or pierce a bottom portion of an ampoule.

Since the second member 84 is made of a robust material, i.e., a metal, it can be formed with a small wall thickness, e.g., in the range from 0.1 to 1 mm. In this way, the force required to open the ampoule can be reduced, thus further simplifying the process of opening the ampoule and enabling a controlled and steady opening process.

The collar 82 of the opening element 80 of the fourth embodiment may be integrally formed with a body of the aerosol generation device, e.g., by injection moulding.

Alternatively, the collar 82 may be attached to the body of the aerosol generation device by fixation means, such as adhesives, clamps, rivets, riveted bolts, screws or the like.

Figure 5:
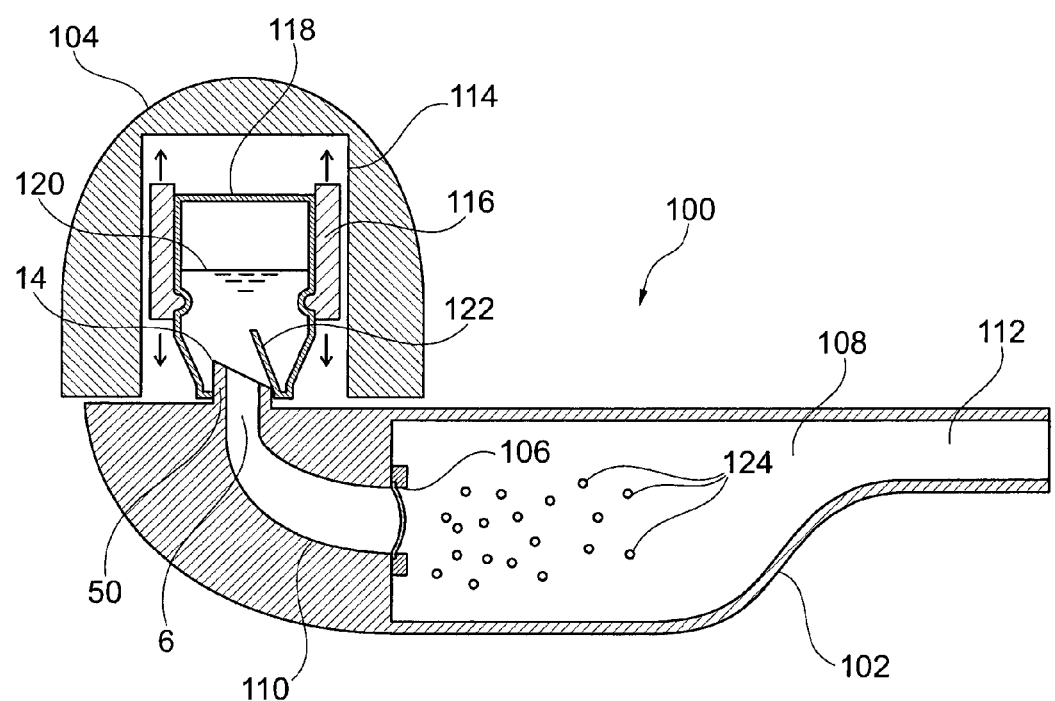
FIG. 5 shows a schematic cross-sectional view of an aerosol delivery device according to an embodiment of the present invention.

FIG. 5 shows a schematic cross-sectional view of an aerosol generation device 100 according to a currently preferred embodiment of the present invention.

The aerosol generation device 100 shown in FIG. 5 comprises a device body 102 and a lid 104. The opening element 50 of the second embodiment shown in FIG. 2 is integrally formed with the device body 102. The device body 102 comprises an aerosol generating element 106, such as a vibrating membrane, arranged within a nebuliser chamber 108, a supply channel 110 for supplying a fluid from the opening element 50 to the aerosol generating element 106 and a mouthpiece 112 to be received in a patient's mouth.

The lid 104 of the aerosol generation device 100 comprises an ampoule holder 114 with a holding part 116 which is movable relative to the opening element 50 in the axial direction of the ampoule holder 114, i.e., the axial direction of the conduit 6 of the opening element 50, as is indicated by the arrows in FIG. 5. An ampoule 118 containing a fluid 120 to be aerosolised is movably held in the ampoule holder 114 by the holding part 116. The ampoule 118 has a bottom wall part 122 which is to be opened by the opening element 50.

In operation of the aerosol generation device 100, the ampoule 118 containing the fluid 120 to be nebulised is first placed within the ampoule holder 114 so as to be held by the holding part 116. At this stage, the ampoule 118 is in a closed state, i.e., in a state, in which the bottom wall part 122 seals the ampoule 118. Subsequently, the lid 104 is placed on the device body 102 so as to close the aerosol generation device 100. Initially, the holding part 116 is in a position remote from the opening element 50 so that the opening element 50 does not come into contact with the bottom wall part 122 of the ampoule 118 when the lid 104 is placed on the device body 102.

Next, the holding part 116 is moved towards the opening element 50, pushing the bottom wall part 122 against the inclined top portion 14 of the opening element 50. The top portion 14 of the opening element 50 breaks open the bottom wall part 122 of the ampoule 118, e.g., at a predetermined breaking point. Upon further movement of the holding part 116 in the direction towards the opening element 50, the opening element 50 fully enters into the ampoule 118, pushing aside the opened bottom wall part 122 and thus bringing the conduit 6 of the opening element 50 into fluid communication with the interior of the ampoule 118.

The fluid 120 contained in the ampoule 118 is guided through the opening element 50 via the conduit 6 into the supply channel 110. Due to the presence of the plate 52 (not shown in FIG. 5; see FIG. 2) inside the conduit 6, a controlled flow of the fluid 120 through the opening element 50 can be ensured, as has been explained in detail above.

The supply channel 110 supplies the fluid from the ampoule 118 to the aerosol generating element 106 which aerosolises the fluid 120, thereby generating an aerosol 124 in the nebuliser chamber 108. The aerosol 124 thus generated is transported into a patient's mouth through the mouthpiece 112. However, the mouthpiece 112 might be replaced by a mask, nosepiece or the like for providing treatment to the nasal cavity and/or the paranasal sinuses of a patient.

Since the opening element 50 with the plate 52, having surfaces 58, 60 which are more wettable than the surface 8 of the collar 2 defining the conduit 6, is used for opening the ampoule 118, a controlled fluid flow from the ampoule 118 through the opening element 50 into the supply channel 110 and further to the aerosol generating element 106 can be ensured. In this way, variations in the doses of the aerosol 124 emitted through the mouthpiece 112 can be reliably prevented, thus enabling a highly effective therapeutic aerosol treatment.

The invention claimed is:

1. An opening element for opening an ampoule in an aerosol generation device, the opening element comprising:

a first member which has a conduit extending therethrough for guiding a fluid contained in the ampoule through the first member, and a second member which is arranged at least partly inside or on the conduit, wherein the second member guides the fluid into the aerosol generation device by gravitational force and wherein an entire surface of the second member has a higher degree of wettability by the fluid than a surface of the first member defining the conduit, wherein the wettability of each surface by the fluid is defined by a contact angle at which a fluid interface meets the surface and wherein the entire surface of the second member has a smaller contact angle than the surface of the first member defining the conduit, wherein the second member partitions the conduit into at least two sections, each extending in an axial direction of the conduit, wherein the axial direction of the conduit is the direction of fluid flow through the conduit, and wherein the at least two sections are arranged next to each other in a direction perpendicular to the axial direction of the conduit.

2. The opening element according to claim 1, wherein at least a portion of the second member extends across the width of the conduit, wherein a plane of the second member is parallel to the axis of the conduit.

3. The opening element according to claim 1, wherein at least a portion of the second member extends along the entire length of the conduit in the axial direction of the conduit.

4. The opening element according to claim 1, wherein the second member has a substantially planar shape.

5. The opening element according to claim 1, wherein the second member at least partly extends along the circumference of the conduit.

6. The opening element according to claim 1, wherein the second member is at least partly in contact with a surface of the first member defining the conduit.

7. The opening element according to claim 1, wherein the second member is resilient and arranged at least partly inside or on the conduit in an at least partly compressed state or locked inside or on the conduit.

8. The opening element according to claim 1, wherein the first member has a substantially cylindrical shape.

9. The opening element according to claim 1, wherein at least a portion of the second member extends through a centre of the conduit with its plane parallel to the axial direction of the conduit.

10. The opening element according to claim 1, wherein the first member has an opening portion for opening the ampoule.

11. The opening element according to claim 1, wherein the second member has an opening portion for opening the ampoule.

12. The opening element according to claim 1, wherein the second member is made of a metal.

13. The opening element according to claim 1, wherein the first member is made of a polymer.

14. The opening element according to claim 1, wherein the first member is made of a first material, wherein the second member is made of a second material, and wherein the second material is different from the first material.

15. The opening element according to claim 14, wherein the second material has a higher degree of wettability by the fluid than the first material.

16. The opening element according to claim 1, wherein the contact angle of the entire surface of the second member is 5° or more smaller than the contact angle of the surface of the first member defining the conduit.

17. The opening element according to claim 1, wherein the contact angle of the entire surface of the second member is 20° or more smaller than the contact angle of the surface of the first member defining the conduit.

18. An aerosol generation device comprising an opening element for opening an ampoule in the aerosol generation device, the opening element comprising:

a first member which has a conduit extending therethrough for guiding a fluid contained in the ampoule through the first member, and a second member which is arranged at least partly inside or on the conduit, wherein the second member guides the fluid into the aerosol generation device by gravitational force and wherein an entire surface of the second member has a higher degree of wettability by the fluid than a surface of the first member defining the conduit, wherein the wettability of each surface by the fluid is defined by a contact angle at which a fluid interface meets the surface and wherein the entire surface of the second member has a smaller contact angle than the surface of the first member defining the conduit, wherein the second member partitions the conduit into at least two sections, each extending in an axial direction of the conduit, wherein the axial direction of the conduit is the direction of fluid flow through the conduit, and wherein the at least two sections are arranged next to each other in a direction perpendicular to the axial direction of the conduit, and wherein the aerosol generation device further comprises an aerosol generating element, wherein the aerosol generating element comprises a vibrating membrane, and wherein the opening element is in fluid communication with the aerosol generating element so as to allow for a fluid flow from the ampoule through the opening element onto the aerosol generating element.

19. The aerosol generation device according to claim 18, wherein the vibrating membrane is a perforated vibrating membrane.

20. The aerosol generation device according to claim 18, further comprising a mouthpiece and/or a mask and/or a nosepiece for delivering an aerosol generated by the aerosol generating element to a patient.

* * * * *